United States Patent
Italiaie et al.

(10) Patent No.: US 10,918,421 B2
(45) Date of Patent: *Feb. 16, 2021

(54) SPINAL IMPLANT SYSTEM AND METHODS OF USE

(71) Applicant: Warsaw Orthopedic, Inc., Warsaw, IN (US)

(72) Inventors: Christel Italiaie, Memphis, TN (US); Jason M. May, St. Johns, FL (US); Larry Thomas McBride, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 8 days.

This patent is subject to a terminal disclaimer.

(21) Appl. No.: 16/405,649

(22) Filed: May 7, 2019

(65) Prior Publication Data

US 2020/0352607 A1 Nov. 12, 2020

(51) Int. Cl.
*A61B 17/70* (2006.01)

(52) U.S. Cl.
CPC ...... *A61B 17/7037* (2013.01); *A61B 17/7032* (2013.01); *A61B 17/7002* (2013.01); *A61B 17/704* (2013.01)

(58) Field of Classification Search
CPC ............ A61B 17/7049; A61B 17/7035; A61B 17/7091; A61B 17/7043; A61B 17/8605; A61B 17/7037; A61B 17/7038; A61B 17/7032; A61B 17/7067; A61B 17/7002; A61B 17/704; A61B 17/683; A61B 17/7005; A61B 17/7076; A61B 17/7082; A61B 17/7034; A61B 17/7086

USPC .................... 606/246–279, 300–328
See application file for complete search history.

(56) References Cited

U.S. PATENT DOCUMENTS

| | | | |
|---|---|---|---|
| 9,566,092 B2 * | 2/2017 | Jackson | A61B 17/7032 |
| 9,993,270 B2 * | 6/2018 | Butler | A61B 17/7035 |
| 10,258,386 B2 | 4/2019 | Butler | |
| 10,335,201 B2 * | 7/2019 | Rezach | A61B 17/7032 |
| 10,687,858 B2 * | 6/2020 | Italiaie | A61B 17/7032 |
| 2007/0135817 A1 * | 6/2007 | Ensign | A61B 17/7037 606/96 |
| 2015/0201972 A1 * | 7/2015 | Doubler | A61B 17/7002 606/266 |
| 2015/0282845 A1 * | 10/2015 | Mirda | A61B 17/7032 606/272 |
| 2017/0245898 A1 | 8/2017 | May et al. | |
| 2018/0110548 A1 | 4/2018 | May et al. | |
| 2018/0116695 A1 * | 5/2018 | Armstrong | A61B 17/705 |
| 2018/0317971 A1 | 11/2018 | Prevost | |

(Continued)

*Primary Examiner* — Pedro Philogene
(74) *Attorney, Agent, or Firm* — Sorell, Lenna & Schmidt, LLP

(57) ABSTRACT

A spinal construct comprises a body defining a first groove. A transverse rod is formed with the body. A first band is disposable in the first groove. A base is connectable with the body and engageable with the first band. The base defines a second groove and a slot. A second band is disposable in the second groove and defines an opening aligned with the slot. A shaft is connectable with the base and engageable with the second band. The shaft is configured to penetrate tissue. The opening is aligned with the slot to facilitate an angular range of movement of the shaft relative to the body. Implants, systems, instruments and methods are disclosed.

20 Claims, 6 Drawing Sheets

(56) References Cited

U.S. PATENT DOCUMENTS

| | | |
|---|---|---|
| 2018/0353220 A1 | 12/2018 | Loke et al. |
| 2019/0183535 A1 | 6/2019 | May et al. |

\* cited by examiner

SPINAL IMPLANT SYSTEM AND METHODS OF USE

TECHNICAL FIELD

The present disclosure generally relates to medical devices for the treatment of spinal disorders, and more particularly to a surgical implant system including a spinal construct and related methods.

BACKGROUND

Spinal pathologies and disorders such as kyphosis, scoliosis and other curvature abnormalities, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, lam inectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a spinal construct is provided. The spinal construct comprises a body defining a first groove. A transverse rod is formed with the body. A first band is disposable in the first groove. A base is connectable with the body and engageable with the first band. The base defines a second groove and a slot. A second band is disposable in the second groove and defines an opening aligned with the slot. A shaft is connectable with the base and engageable with the second band. The shaft is configured to penetrate tissue. The opening is aligned with the slot to facilitate an angular range of movement of the shaft relative to the body. In some embodiments, implants, systems, instruments and methods are disclosed.

In one embodiment, the spinal construct comprises a body defining a first groove and including a transverse rod formed therewith. A first band is disposable in the first groove. A part is disposed within the body. A base is connectable with the body and engageable with the first band. The base defines a second groove and a slot. A second band is disposable in the second groove and defines an opening aligned with the slot. A shaft is connectable with the base and engageable with the second band. The shaft is configured to penetrate tissue. The opening is aligned with the slot to facilitate an angular range of movement of the shaft relative to the body. A third band is disposed with the base. The part is engageable with the third band to fix the base with the shaft.

In one embodiment, the spinal construct comprises a body having a spinal rod formed therewith. The body defines a first groove. A first band is disposable in the first groove. A base is connectable with the body and engageable with the first band. The base defines a second groove and a slot. A second band is disposable in the second groove and defines an opening aligned with the slot. A screw shaft is connectable with the base and engageable with the second band in a non-instrumented assembly. The opening is aligned with the slot and the screw shaft is movable in the slot to a selected angulation including an angular range of about 30 through about 60 degrees relative to a longitudinal axis of the body.

BRIEF DESCRIPTION OF THE DRAWINGS

The present disclosure will become more readily apparent from the specific description accompanied by the following drawings, in which.

DETAILED DESCRIPTION

Figure 1:
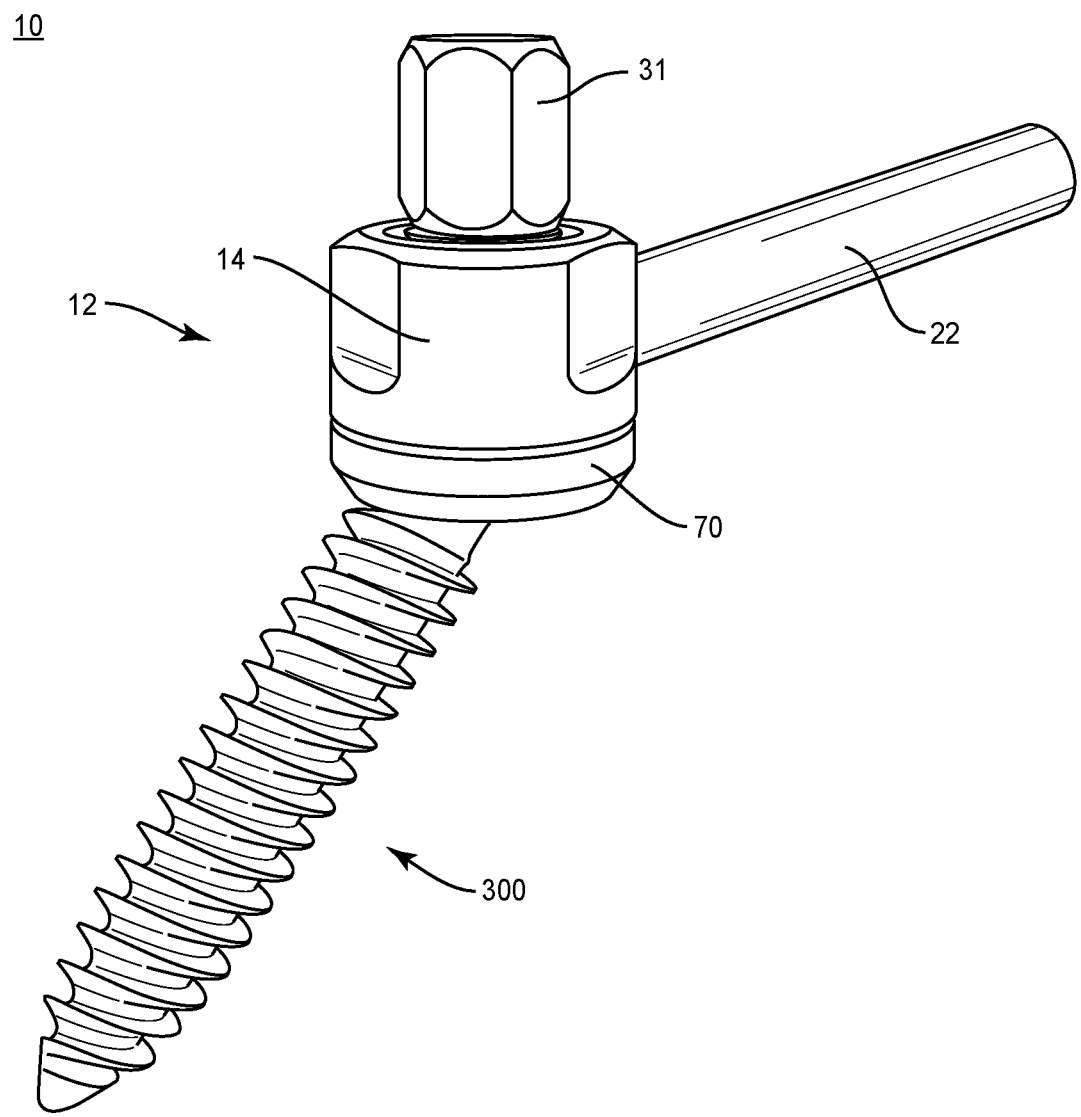
FIG. 1 is a perspective view, partially cut away, of components of one embodiment of a spinal implant system in accordance with the principles of the present disclosure.

The exemplary embodiments of a surgical system and related methods of use disclosed are discussed in terms of medical devices for the treatment of musculoskeletal disorders and more particularly, in terms of a spinal implant system including a spinal construct. In some embodiments, a spinal implant system includes a spinal construct having a spinal rod having a body connectable with a screw shaft. In some embodiments, the spinal implant system includes a selectively coupled spinal construct system that allows for assembly during surgery and/or with operating room back-table assembly without use of instrumentation. In some embodiments, the systems and methods of the present disclosure are employed with a spinal joint fusion or fixation procedure, for example, with a cervical, thoracic, lumbar and/or sacral region of a spine.

In some embodiments, the present spinal implant system comprises a spinal implant, such as, for example, a spinal construct having a screw shaft that is engageable with tissue surfaces of one or more vertebral levels. In some embodiments, the spinal implant system includes a selectively coupled spinal construct system that allows for a biased angle configuration. In some embodiments, the spinal construct includes a body with a spinal rod extending therefrom and being connectable with a screw shaft. In some embodiments, the connection of the body and the screw shaft provide a range of angulation to allow the body and/or spinal rod to be positioned in a relaxed or non-stressed orientation relative to the screw shaft. In some embodiments, this configuration allows the components of adjacent spinal constructs, which may include bone screws and/or spinal rods, to be disposed in a relatively parallel orientation. In some embodiments, the spinal implant system comprises a spinal construct including one or more components configured for angulation in a cephalad-caudal direction of a patient body. In some embodiments, the spinal construct includes a body with a spinal rod extending therefrom and being connectable with a screw shaft in a non-instrumented assembly. In some embodiments, this configuration avoids a surgical step of seating a separate spinal rod with an implant receiver.

In some embodiments, the spinal construct body is connectable with a screw shaft configured for angulation in a range of approximately 0 through approximately 40 degrees relative to a patient body. In some embodiments, the spinal construct comprises a body with a spinal rod extending therefrom, a crown, a base, a head-base ring, a crown ring, and bone screw shaft ring and a bone screw shaft. In some embodiments, the crown includes a temporary retention slot and/or ramp. In some embodiments, a head of the bone screw shaft includes a base retention slot. In some embodiments, the spinal rod extends from the body at an angle in a range of approximately 0 through approximately 25 degrees relative to the body. In some embodiments, the spinal rod extends at an angle of 15 degrees relative to a transverse axis of the body.

In some embodiments, the spinal construct body includes ring slots to facilitate a manual engagement of the body and the screw shaft. In some embodiments, the base includes a biased angle slot. In some embodiments, the base includes a screw shaft ring slot configured to resist and/or prevent the screw ring from rotation.

In some embodiments, the spinal construct comprises a crown having a flat top, knurled features and mating features to facilitate positioning with the screw head. In some embodiments, the crown includes a cavity configured for disposal of the screw shaft. In some embodiments, the crown includes planar surfaces configured for a keyed connection with the screw head. In some embodiments, the planar surfaces are utilized to position the biased angle feature on the base.

In some embodiments, the screw shaft ring includes a thickness. In some embodiments, the screw shaft ring includes two chamfers. In some embodiments, the screw shaft ring includes a cavity. In some embodiments, the cavity is configured to facilitate axial translation of the screw shaft ring relative to the base. In some embodiments, the cavity is engageable with the base to resist and/or prevent rotation of the screw shaft ring such that the screw shaft ring slot is positioned in alignment with the biased angle slot of the base. In some embodiments, the screw shaft ring slot is configured to allow angulation of the screw shaft at approximately 40 degrees. In some embodiments, the screw shaft ring slot and the biased angle slot can be rotated 360 degrees about the screw shaft.

In some embodiments, the screw shaft includes a base having notches configured for engagement with ends of the screw shaft ring to resist and/or prevent disengagement of the screw shaft ring from the base. In some embodiments, engagement of the screw shaft ring with surfaces of the notches allows for axial translation of the screw shaft ring relative to the base while resisting and/or preventing rotation of the screw shaft ring relative to the base to maintain alignment of an opening of the bone screw shaft ring with the biased angle slot.

In some embodiments, the spinal implant system comprises a modular spinal construct. In some embodiments, the spinal implant system comprises a modular spinal construct including screw shaft assemblies and body/spinal rod assemblies that may be joined together during manufacturing or intra-operatively, such as, for example, during a surgical procedure in an operating room.

In some embodiments, the spinal construct is configured for assembly without the use of an instrument, such as, for example, a practitioner, surgeon and/or medical staff utilizes their hands for assembly. In some embodiments, the system requires minimal force to attach a body and a screw shaft assembly in-situ thereby reducing a pre-load on the vertebrae, such as, for, example, the pedicle.

In some embodiments, the present disclosure may be employed to treat spinal disorders such as, for example, degenerative disc disease, disc herniation, osteoporosis, spondylolisthesis, stenosis, scoliosis, kyphosis and other curvature abnormalities, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-7, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 2:
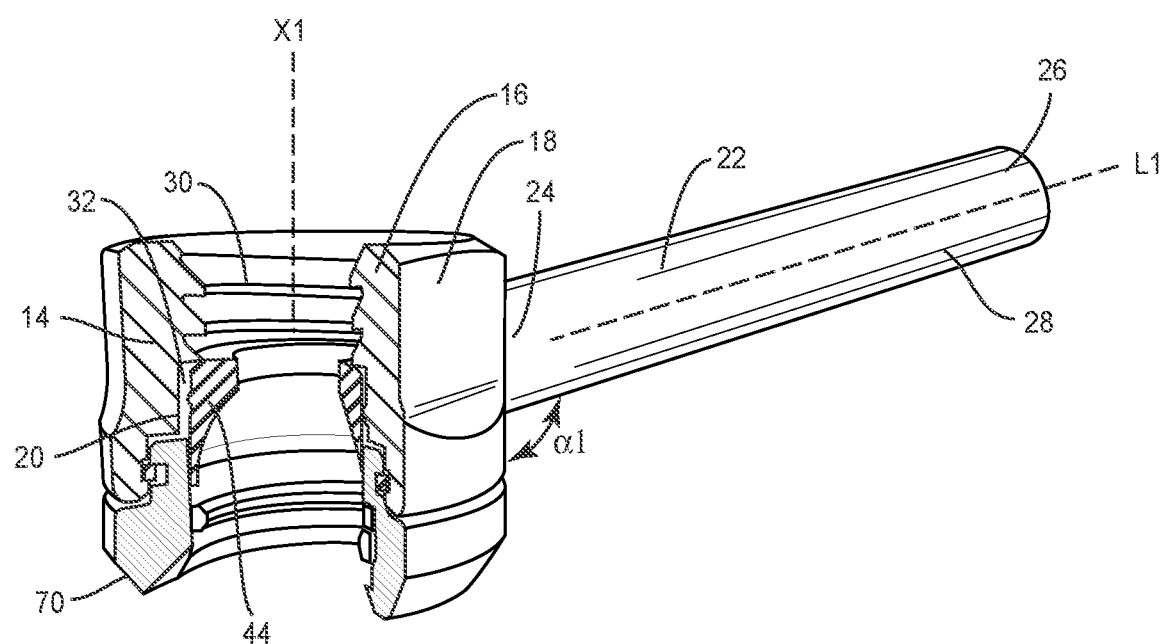
FIG. 2 is a perspective cut away view of components of the system shown in FIG. 1.

Spinal implant system 10 includes a spinal implant, such as, for example, a spinal construct 12. Spinal construct 12 comprises a body 14 connectable with a bone screw 300, as described herein. Body 14 includes a wall 16, as shown in FIG. 2. Wall 16 in various embodiments has a substantially circular profile or cross section, and extends along an axis X1, as shown in FIG. 2. In some embodiments, wall 16 extends in alternative configurations relative to axis X1, such as, arcuate, offset, staggered and/or angled portions. Wall 16 includes an outer surface 18 and an inner surface 20.

A spinal rod 22 is formed with body 14. Rod 22 extends from surface 18 along an axis L1. Rod 22 extends transverse to axis X1. In some embodiments, rod 22 may extend in alternate orientations relative to axis X1, such as, for example, arcuate, tapered, perpendicular, and/or other angular orientations such as acute or obtuse, co-axial and/or may be offset or staggered. Rod 22 extends between a first end 24 and a second end 26. In some embodiments, rod 22 may have various cross-section configurations, such as, for example, circular, oval, oblong, polygonal, irregular, uniform, non-uniform, variable, offset and/or tapered. Rod 22 includes a surface 28 configured for connection with a receiver of one or a plurality of bone fasteners 500 (FIGS. 8 and 9), as described herein.

Rod 22 extends such that axis L1 is disposed at an angle α1 relative to axis X1. In some embodiments, angle α1 is in a range of about 0 degrees to about 25 degrees. In some embodiments, angle α1 is about 15 degrees. In some embodiments, rod 22 can be offset in various axial, planar and/or other orientations, such as, for example, a transverse plane, a coronal plane, or a sagittal plane, or perpendicular or parallel to axis X1.

In some embodiments, rod 22 is monolithically formed with body 14. In some embodiments, rod 22 is integrally connected with body 14 by welding or other connection technique. In some embodiments, rod 22 is integrally connected with body 14 by fastening elements and/or instruments to facilitate connection.

A portion of inner surface 20 includes a thread form 30 configured for engagement with a coupling member, such as, for example, a setscrew 31, to fix body 14 with bone screw 300. In some embodiments, surface 20 may be disposed with the coupling member in alternate fixation configurations, such as, for example, friction fit, pressure fit, locking protrusion/recess, locking keyway and/or adhesive.

Figure 3:
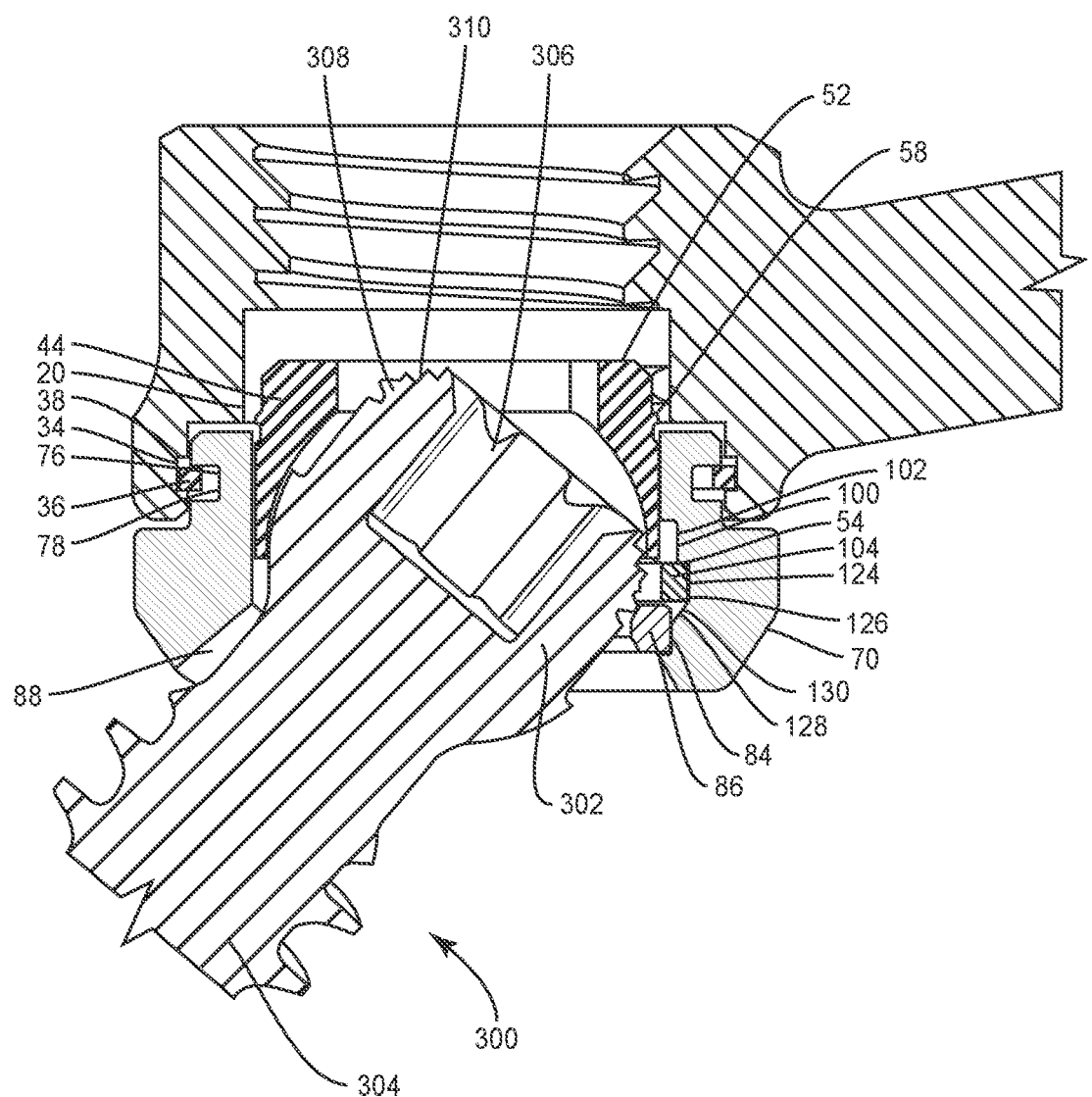
FIG. 3 is an enlarged cross-section view of components of the system shown in FIG. 1.

A portion of inner surface 20 defines a cavity 32, called out in FIG. 2. Cavity 32 is configured for disposal of a head 302 of bone screw 300, as shown in FIGS. 1 and 3. Cavity 32 has a substantially circular profile or cross section in various embodiments. In some embodiments, all or only a portion of cavity 32 has alternative cross-sectional configurations, such as closed, V-shaped, W-shaped, oval, U-shaped, oblong, polygonal, irregular, uniform, non-uniform, offset, staggered, and/or tapered.

Surface 20 defines a cavity, such as, for example, a groove 34. Groove 34 is configured for disposal of a band, such as, for example, a circumferential ring 36, as shown in FIG. 3. Groove 34 includes a circumferential channel 38 that accommodates expansion of ring 36. In various embodiments, ring 36 includes a circumference that extends between ends of ring 36. In some embodiments, the ends do not meet, defining a gap therebetween. In some embodiments, the gap is sized such that the gap has a thickness that is less than the height and/or the width of the thickness. In some embodiments, upon disposal of ring 36 within groove 34, upper and lower surfaces of groove 34 resists and/or prevents axial translation, proximally and distally, of ring 36 relative to axis X1.

Ring 36 is in various embodiments expandable and resilient between (i) a contracted and/or capture orientation, and (ii) an expanded orientation, as described herein. Ring 36 facilitates manual assembly of body 14 with a base 70 in a non-instrumented assembly, as described herein. In some embodiments, ring 36 is expandable and resilient between a contracted and/or capture orientation and an expanded orientation for assembly of body 14 with base 70.

Body 14 is configured for disposal of a part, such as, for example, a crown 44, as described herein. In some embodiments, all or only a portion of surface 40 has alternate surface configurations, such as, for example, rough, arcuate, undulating, mesh, porous, semi-porous, dimpled and/or textured. Crown 44 is configured for disposal within cavity 32 and engagement with surface 20.

Figure 4:
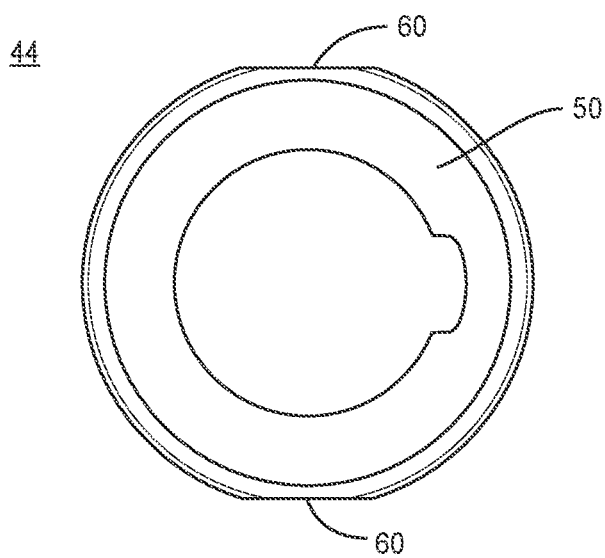
FIG. 4 is a top view of components of one embodiment of a spinal implant system in accordance with the principles of the present disclosure.

Crown 44 includes a wall 50 having an end surface 52 and an end surface 54, as shown in FIG. 4. The crown includes a surface 56 is configured to define at least a portion of cavity 32. Surface 56 defines a curved portion of crown 44 configured for disposal of head 302. In some embodiments, all or only a portion of surface 56 has alternate cross-sectional configurations, such as, for example, oval, oblong triangular, square, polygonal, irregular, uniform, non-uniform, offset, staggered, and/or tapered. Wall 50 defines a body engagement portion, such as, for example, a flange 58 configured for a provisional mating engagement with a portion of surface 20.

In some embodiments, crown 44 includes planar surfaces, such as, for example, flats 60, as shown in FIG. 4. Flats 60 engage surface 40 in a keyed connection to resist and/or prevent rotation of crown 44 relative to body 14. In some embodiments, engagement of flats 60 and surface 40 prevents rotation of crown 44 relative to body 14 and allows axial translation of crown 44 relative to body 14.

Crown 44 is configured for translation within body 14 along surface 20. Translation of crown 44 causes surface 54 to engage a ring 104, as described herein. Surface 54 is disposed adjacent ring 104 such that axial translation of crown 44 causes crown 44 to displace ring 104 from a groove 102, as described herein. Ring 104 is disengageable from groove 102 and surface 54 drives ring 104 from groove 102. As such, ring 104 is movable between the contracted orientation and the expanded interference orientation in groove 124, as described herein, to prevent migration of a ring 86 from a groove 84 into a groove 124 for fixed connection of the components of spinal construct 12. Surface 54 is positioned with ring 104 to resist and/or prevent displacement of ring 104 from groove 124.

Bone screw 300 includes a base 70. Base 70 includes a wall 72, which has a surface 74 that defines a cavity 75. Cavity 75 is configured for disposal of head 302. Surface 74 facilitates engagement of head 302 with base 70 via a pressure and/or force fit connection. In some embodiments, surface 74, referenced in FIG. 5, facilitates a non-instrumented assembly with base 70 and head 302 via an expandable ring 86, as described herein. In some embodiments, base 70 may be disposed with head 302 in alternate fixation configurations, such as, for example, friction fit, pressure fit, locking protrusion/recess, locking keyway and/or adhesive. In some embodiments, base 70 is configured for rotation relative to head 302. In some embodiments, base 70 is configured for rotation in a range of 360 degrees relative to head 302 to facilitate positioning of a shaft 304 of the bone screw 300 with tissue. In some embodiments, base 70 is configured for selective rotation in range of 360 degrees relative to and about head 302 such that shaft 304 is selectively aligned for rotation in a plane relative to body 14.

Wall 72 includes a surface 76 that defines a cavity, such as, for example, a groove 78, as shown in FIG. 3. Groove 78 is configured for disposal of ring 36 to prevent displacement of ring 36 from channel 38 and to permanently fix base 70 with body 14, as shown in FIG. 3, forming a base/body assembly 70/14. For example, alignment of groove 78 with channel 38 allows ring 36 to resiliently contract to the capture orientation, for disposal of ring 36 within groove 78 and channel 38. Ring 36 is fixed within channel 38 and groove 78. The surfaces of groove 78 resist and/or prevent disengagement of ring 36 from channel 38 and groove 78 to permanently assemble base 70 with body 14.

Figure 5:
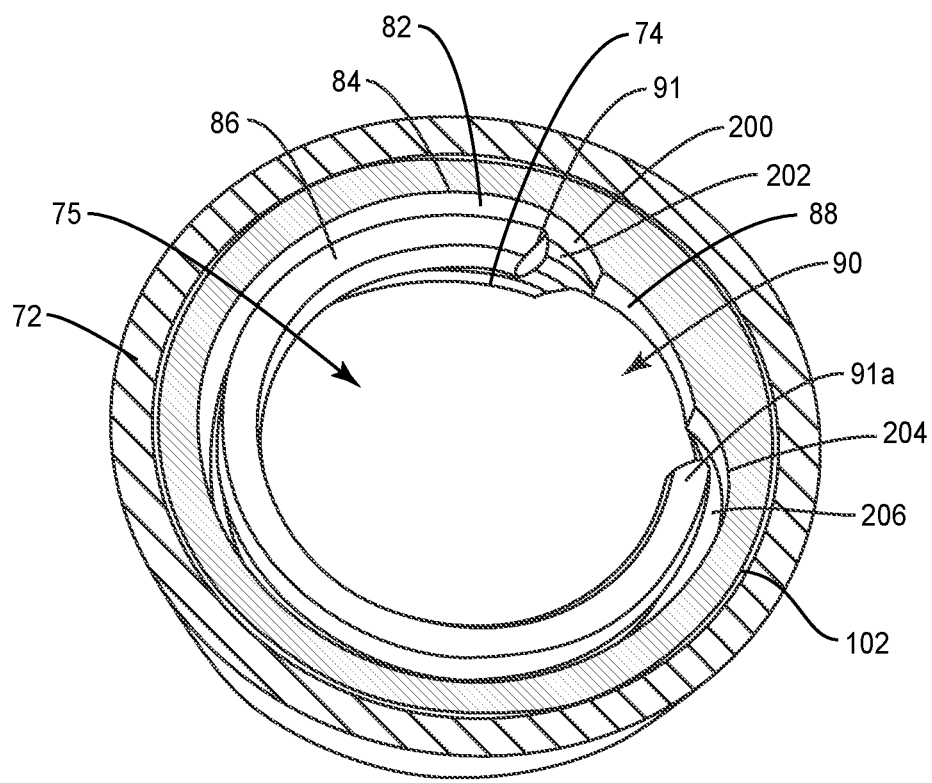
FIG. 5 is a perspective view of components of one embodiment of a spinal implant system in accordance with the principles of the present disclosure.

Base 70 includes a surface 82, as shown in FIG. 5. Surface 82 defines a cavity, such as, for example, a groove 84. Groove 84 is configured for disposal of a band, such as, for example, a circumferential screw shaft ring 86, as described herein. In some embodiments, groove 84 extends about all or a portion of surface 82.

Figure 7:
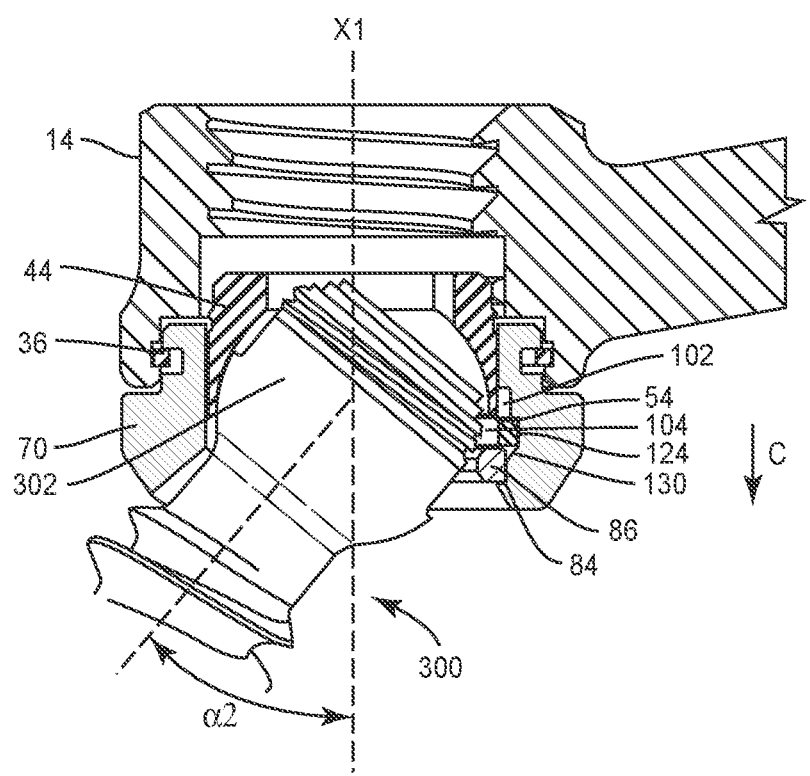
FIG. 7 is a cross-section view of components of one embodiment of a spinal implant system in accordance with the principles of the present disclosure.

An inner surface of wall 72 defines a slot, such as, for example a recess 88, as shown in FIG. 3. Recess 88 is configured for disposal of screw shaft 304. In some embodiments, recess 88 is arcuate and/or concavely curved such that screw shaft 304 is disposable therein for movement of screw shaft 304 at an angle α2 as shown in FIG. 7, to facilitate a biased angle configuration at a selected angle. In some embodiments, angle α2 includes a selected angle in an angular range of about 30 through about 60 degrees. In some embodiments, angle α2 is about 40 degrees relative to axis X1. In some embodiments, angulation of screw shaft 14 includes disposing body 14 at a sharp and/or acute angle α2 relative to screw shaft 14, as shown in FIG. 7, as described herein. For example, head 302 is positionable with recess 88 such that upon engagement with tissue, body 14 can be disposed in a non-stressed and/or relaxed configuration to facilitate engaging rod 22 with bone fastener 500, as described herein.

Ring 86 is configured to fix screw shaft 304 with base 70. Ring 86 includes a circumference that defines an opening 90, as shown in FIG. 5. Opening 90 is disposed between mating surfaces, such as, for example, ends 91, 91a of ring 86. Opening 90 is configured for alignment with recess 88, as shown in FIG. 5. Alignment of opening 90 and recess 88 facilitates movement of screw shaft 14 relative to body 14 in the angular range of motion, as described herein.

Groove 84 includes a surface 200 that defines a mating surface, such as, for example, a notch 202, as shown in FIG. 5. Groove 84 includes a surface 204 that defines a mating surface, such as, for example, a notch 206. Notches 202, 206 are disposed on opposite sides of recess 88. End 91 is configured for disposal with notch 202 and end 91*a* is configured for disposal with notch 206, as shown in FIG. 5. In the expanded orientation, ends 91, 91*a* engage surfaces 200, 204 to fix ring 86 with base 70 for assembly, as described herein. Surfaces 200, 204 resist and/or prevent disengagement of ring 86 from base 70. Engagement of ends 91, 91*a* with surfaces 200, 204 of notches 202, 206 allows for axial translation of ring 86 relative to base 70 as screw shaft 304 is engaged with base 70, as described herein. Ends 91, 91*a* engage surfaces 200, 204 to resist and/or prevent rotation of ring 86 relative to base 70 to maintain alignment of opening 90 and recess 88.

Base 70 includes groove 102, as described herein. Groove 102 is configured for disposal of a circumferential ring 104. Ring 104 is engageable with ring 86 to facilitate fixation of base 70 with screw shaft 304, as described herein. Ring 104 includes a circumference that extends between ends of ring 104. In some embodiments, the ends define an opening, such as, for example, a gap. In some embodiments, the gap is sized such that the gap has a thickness that is less than the height and the width. In some embodiments, the gap is sized to allow ring 104 to engage a surface 100 of groove 102 by contracting circumferentially.

Base 70 includes groove 124 configured for disposal of ring 86 and/or ring 104 to facilitate assembly and/or fixation of base 70 with screw shaft 304, as described herein. In some embodiments, groove 124 extends about all or a portion of surface 122. Groove 124 includes a circumferential channel 126 that accommodates expansion of ring 86 and/or ring 104, as described herein. Grooves 84, 102, 124 are disposed in a serial orientation along axis X1, as shown in FIG. 3. In some embodiments, grooves 84, 102, 124 are disposed in spaced apart relation.

A surface 128 is disposed between groove 124 and groove 84. Surface 128 is disposed at an angle relative to axis X1 to define a ramp 130. Ramp 130 is selectively inclined to facilitate translation of ring 86 between groove 84 and groove 124, as described herein. In one example, ring 86 is engaged with screw shaft 304 for translation such that ring 86 slides along ramp 130, which directs and/or guides ring 86 from groove 84 into groove 124 and expands into a provisional capture orientation with screw shaft 14. In another example, ring 86 is engaged with ring 104 for translation such that ring 86 slides along ramp 130, which directs and/or guides ring 86 from groove 124 into groove 84, and contracts for fixed connection of the components of spinal construct 12 including permanent capture of body 14 and screw shaft 304. In some embodiments, surface 130 is oriented substantially perpendicular to axis X1.

Ring 86 is resiliently biased to a contracted and/or capture orientation within groove 84, and expandable to an expanded orientation within groove 124, for provisional capture of screw shaft 304 with body 14, as described herein. Ring 86 is expandable from the contracted and/or capture orientation to the expanded orientation for assembly of screw shaft 304 with body 14, as described herein.

Ring 104 is disposable in a contracted orientation within groove 102 and resiliently biased to an expanded interference orientation within groove 124. In the interference orientation, ring 104 is disposed in groove 102 and adjacent to ring 86 for abutting and/or contacting engagement therewith to resist and/or prevent translation of ring 86 from groove 84 into groove 102, and fixed connection of the components of spinal construct 12 including permanent capture of base 70 and screw shaft 304, as described herein.

Bone screw 300 includes head 302 and screw shaft 304, as described herein. Screw shaft 304 is configured to penetrate tissue, such as, for example, bone. In some embodiments, screw shaft 304 includes an outer surface having an external thread form. In some embodiments, the external thread form may include a single thread turn or a plurality of discrete threads. Head 302 includes a tool engaging portion 306 configured to engage a surgical tool or instrument, as described herein. In some embodiments, portion 306 includes a hexagonal cross-section to facilitate engagement with a surgical tool or instrument, as described herein. In some embodiments, portion 306 may have alternative cross-sections, such as, for example, rectangular, polygonal, hexalobe, oval, or irregular. In some embodiments, head 302 includes a surface 308 that defines a plurality of ridges 310 to improve purchase of head 302 with crown 44. Head 302 is configured for attachment with base 70 and/or body 14, as described herein.

In some embodiments, base 70 and/or body 14 is manually engageable with bone screw 300 in a non-instrumented assembly, as described herein. In some embodiments, manual engagement and/or non-instrumented assembly of base 70 and/or body 14 and bone screw 300 includes coupling without use of separate and/or independent instrumentation engaged with bone screw 300 components to effect assembly. In some embodiments, manual engagement and/or non-instrumented assembly includes a practitioner, surgeon and/or medical staff grasping base 70 and/or body 14 and bone screw 300 and forcibly assembling the components. In some embodiments, manual engagement and/or non-instrumented assembly includes a practitioner, surgeon and/or medical staff grasping base 70 and/or body 14 and bone screw 300 and forcibly snap fitting the components together, as described herein. In some embodiments, manual engagement and/or non-instrumented assembly includes a practitioner, surgeon and/or medical staff grasping base 70 and/or body 14 and bone screw 300 and forcibly pop fitting the components together and/or pop fitting base 70 and/or body 14 onto bone screw 300, as described herein. In some embodiments, a force in a range of 2-50 N is required to manually engage base 70 and/or body 14 and bone screw 300 and forcibly assemble the components. For example, a force in a range of 2-50 N is required to snap fit and/or pop fit assemble base 70 and/or body 14 and bone screw 300. In some embodiments, a force in a range of 5-10 N is required to manually engage base 70 and/or body 14 and bone screw 300 and forcibly assemble the components. For example, a force in a range of about 5 to about 10 N is required to snap fit and/or pop fit assemble base 70 and/or body 14 and bone screw 300. In some embodiments, bone screw 300 is manually engaged with base 70 and/or body 14 in a non-instrumented assembly, as described herein, such that removal of base 70 and/or body 14 and bone screw 300 requires a force and/or a pull-out strength of at least 5000 N. In some embodiments, this configuration provides manually engageable components that are assembled without instrumentation, and subsequent to assembly, the assembled components have a selected pull-out strength and/or can be pulled apart, removed and/or separated with a minimum required force. In some embodiments, spinal implant system 10 comprises a spinal implant kit, as described herein, which includes a plurality of bone screws 300 and/or bodies 14 connectable with base 70.

Base 70 is connected with body 14 in a non-instrumented assembly to form base/body assembly 70/14. In some embodiments, base 70 is assembled with bone screw 300 prior to body 14 being assembled with base 70. Ring 86 is disposed with base 70. Ring 86 is disposed with base 70 and fixed with base 70 via engagement of ends 91, 91a with notches 202, 206. Base 70 is engaged with body 14. Ring 36 is expandable and resilient between a contracted and/or capture orientation, and an expanded orientation within groove 78 and channel 38 to permanently fix base 70 with body 14. The surfaces of groove 78 resist and/or prevent disengagement of ring 36 from channel 38 and groove 78 to permanently assemble base 70 with body 14.

Figure 6:
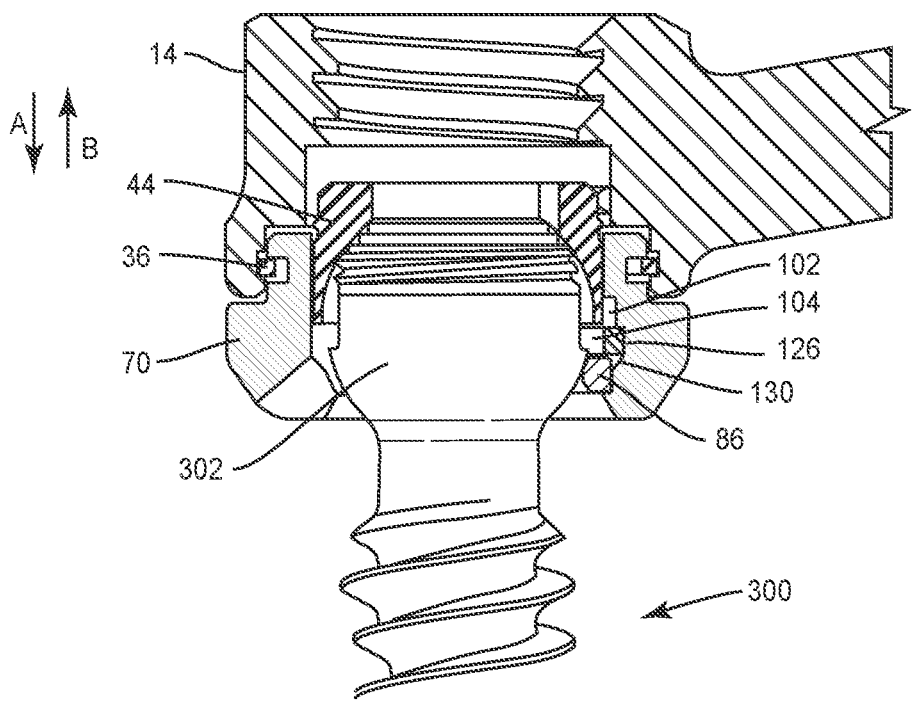
FIG. 6 is a cross-section view of components of one embodiment of a spinal implant system in accordance with the principles of the present disclosure.

Bone screw 300 is manually engageable, as described herein, with base/body assembly 70/14, as shown in FIGS. 6 and 7. Base/body assembly 70/14 is assembled with bone screw 300 by translating base/body assembly 70/14, in a direction shown by arrow A in FIG. 6. Engagement of head 302 with base/body assembly 70/14 causes ring 86 to translate, in a direction shown by arrow B in FIG. 6, such that ring 86 is positionable and allowed to expand into groove 124 to an expanded orientation, as described herein. Engagement of head 302 with an inner surface of ring 86 causes ring 86 to expand and slide along ramp 130 into channel 126. As head 302 translates further into base/body assembly 70/14, ring 86 passes over head 302 and resiliently contracts about head 302 within channel 126 to provisionally capture screw shaft 304.

Crown 44 is manipulated, for example, via engagement of coupling member 31 with body 14 or by surgical instrument, to translate crown 44, in a direction shown by arrow C in FIG. 7. Surface 54 engages ring 104 such that ring 104 is displaced from groove 102, as shown in FIG. 7. Ring 104 translates and engages ring 86 driving ring 86 from groove 124 into groove 84. Ring 86 axially translates along base 70 and/or slides along ramp 130 into groove 84. Ring 104 translates into groove 124 and resiliently expands to an expanded, interference orientation, as described herein. Ring 104 is oriented for abutting and/or contacting engagement with ring 86 to resist and/or prevent translation of ring 86 from groove 84 into groove 124, and fixed connection of the components of spinal construct 12 including permanent capture of base/body assembly 70/14 and bone screw 300. Surface 54 is positioned with ring 104 to resist and/or prevent displacement of ring 104 from channel 126.

In assembly, operation and use, spinal implant system 10, similar to other systems and methods described herein, is employed with a surgical procedure for treating disorders of the spine, such as those described herein. In some embodiments, one or all of the components of spinal implant system 10 can be delivered as a pre-assembled device or can be assembled in situ.

A surgical treatment including spinal implant system 10 can be used for correction and alignment in stabilization of a treated section of vertebrae V. In an exemplary use, a medical practitioner obtains access to a surgical site including vertebrae V via a posterior surgical approach. In some embodiments, the surgical site may be accessed in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area.

An incision is made in the body of a patient and a cutting instrument (not shown) creates a surgical pathway for delivery and implantation of components of spinal implant system 10 with vertebrae V. A preparation instrument (not shown) can be employed to prepare tissue surfaces of vertebrae V, as well as for aspiration and irrigation of a surgical region.

Figure 8:
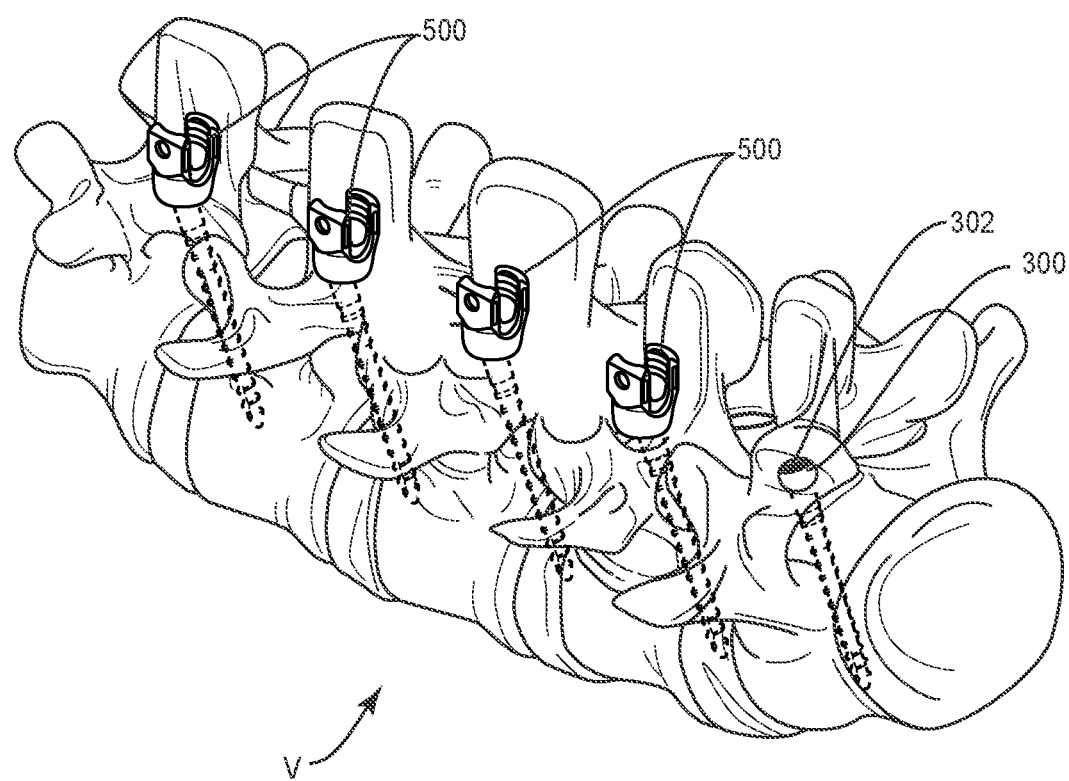
FIG. 8 is a perspective view of components of one embodiment of a spinal implant system disposed with vertebrae in accordance with the principles of the present disclosure.
Figure 9:
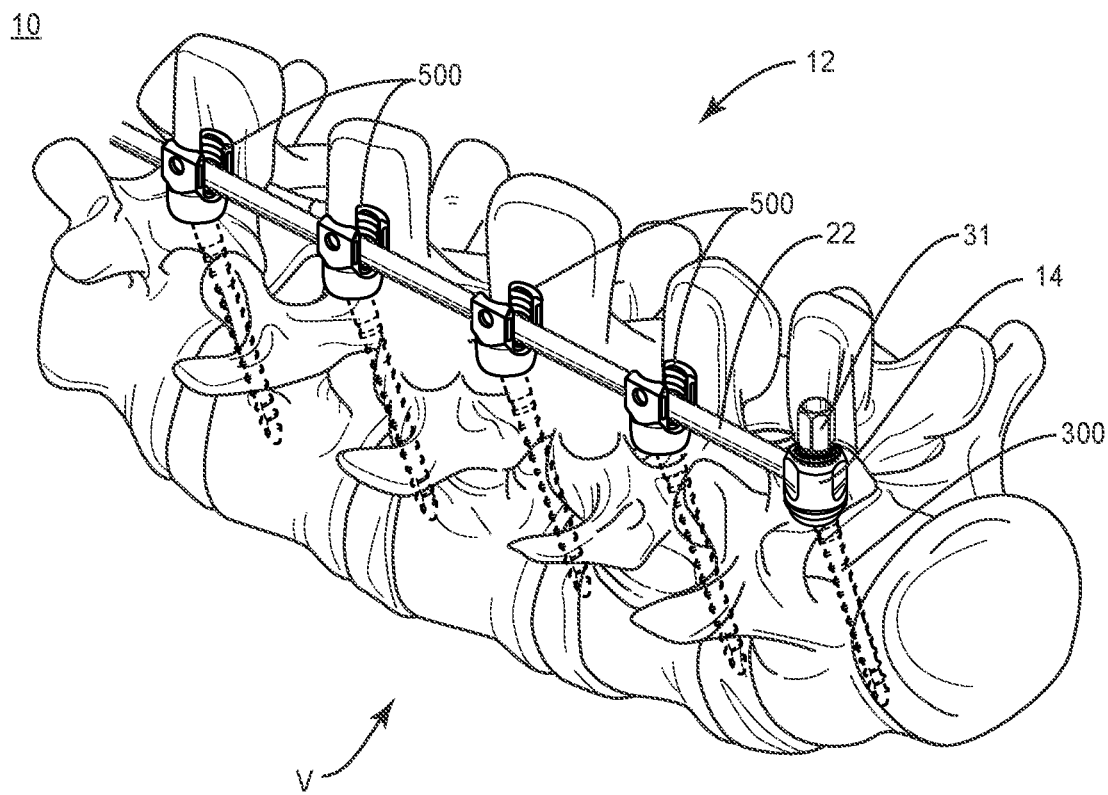
FIG. 9 is a perspective view of components of one embodiment of a spinal implant system disposed with vertebrae in accordance with the principles of the present disclosure.

Spinal implant system 10 includes spinal construct 12, as described herein, and bone fasteners 500, which are delivered to the surgical site for disposal with vertebrae V in connection with the surgical procedure. In some embodiments, one or more bone fasteners 500 are disposed in a serial and/or substantially linear orientation along vertebrae V, as shown in FIGS. 8 and 9. In some embodiments, one or more bone fasteners 500 are disposed with vertebrae V in alternate orientations relative to each other, such as, for example, parallel, perpendicular, adjacent, co-axial, co-planar, arcuate, offset, staggered, transverse, angular and/or relative posterior/anterior orientations and/or at alternate vertebral levels.

Pilot holes are made in vertebrae V. Spinal construct 12 is assembled in situ or prior to implant, as described herein. In some embodiments, spinal construct 12 components may be assembled in a non-instrumented assembly on a back table of an operating room during a surgical procedure, as described herein. In some embodiments, spinal construct 12 is assembled in an instrumented assembly.

Bone screw 300 is aligned with the pilot holes and fastened with the tissue of vertebrae V. In some embodiments, the bony structures of vertebrae V are disposed such that placement of spinal construct 12 includes an implant trajectory with bone screw 300 being angled in a cephalad-caudal orientation for engagement with tissue. Such an implant trajectory of bone screw 300 may include disposing body 14 at a sharp and/or acute angle α2 relative to bone screw 300 for connection of rod 22 with bone fasteners 500, as described herein. As such, the assembled components of spinal construct 12, as described herein, facilitate placement of bone screw 300 along a selected implant trajectory and orientation of body 14 in a non-stressed and/or relaxed configuration to facilitate disposal of spinal rod 22 with bone fasteners 500. For example, with bone screw 300 engaged with vertebral tissue, body 14 is manipulated relative to bone screw 300 and/or to a selected angular orientation relative to bone screw 300, for example, for disposal of bone screw 300 with recess 88/opening 90. In some embodiments, body 14 is manipulable relative to bone screw 300 to an angular limit that includes engagement of bone screw 300 with wall 72. Opening 90 and recess 88 are aligned, as described herein, to allow bone screw 300 to be selectively angled within opening 90 and recess 88 to angle α2, as described herein. The selective angular positioning of bone screw 300 within opening 90 and recess 88 facilitates orienting body 14 for disposal of rod 22 with bone fasteners 500. In some embodiments, the assembled components of spinal construct 12, as described herein, facilitate parallel orientation of lateral and contra-lateral bodies 14 and/or bone fasteners 500 engaged with vertebral tissue for receiving rods 22.

Rod 22 is shaped, contoured and/or bent to a selected configuration for a selected final lordosis of vertebrae V as attached with bone fasteners 500 in connection with the surgical procedure. Body 14 is delivered to the surgical site and oriented for alignment with the implant cavities of bone fasteners 500. In some embodiments, this configuration avoids a surgical step of seating rod 22 with bone fasteners 500. Coupling members 502 are engaged with bone fasteners 500 and coupling member 31 is engaged with body 14 to fix rod 22 with vertebrae V.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

Upon completion of the procedure, the non-implanted components, surgical instruments and assemblies of spinal implant system 10 are removed and the incision is closed. In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In some embodiments, spinal implant system 10 can include one or a plurality of spinal constructs 12 described herein and/or fixation elements, which may be employed with a single vertebral level or a plurality of vertebral levels. In some embodiments, spinal constructs 12 may be engaged with vertebrae in various orientations, such as, for example, series, parallel, offset, staggered and/or alternate vertebral levels. In some embodiments, spinal constructs 12 may be configured as multi-axial screws, sagittal angulation screws, pedicle screws, mono-axial screws, uni-planar screws, fixed screws, anchors, tissue penetrating screws, conventional screws, expanding screws. In some embodiments, spinal constructs 12 may be employed with wedges, anchors, buttons, clips, snaps, friction fittings, compressive fittings, expanding rivets, staples, nails, adhesives, posts, connectors, fixation plates and/or post.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
   a body defining a first groove;
   a transverse rod formed with the body;
   a first band disposable in the first groove;
   a base connectable with the body and engageable with the first band, the base defining a second groove and a slot;
   a second band disposable in the second groove and defining an opening aligned with the slot; and
   a shaft connectable with the base and engageable with the second band, the shaft being configured to penetrate tissue, the opening being aligned with the slot to facilitate an angular range of movement of the shaft relative to the body.

2. A spinal construct as recited in claim 1, wherein the rod extends from the body at an angle in a range of approximately 0 through approximately 25 degrees relative to the body.

3. A spinal construct as recited in claim 1, wherein the rod extends from the body at an angle of about 15 degrees relative to a transverse axis of the body.

4. A spinal construct as recited in claim 1, wherein the shaft is disposable in the slot at a selected angulation relative to the body.

5. A spinal construct as recited in claim 4, wherein the selected angulation includes an angular range of about 30 through about 60 degrees relative to a longitudinal axis of the body.

6. A spinal construct as recited in claim 5, wherein the selected angulation includes an angle of about 40 degrees relative to the longitudinal axis.

7. A spinal construct as recited in claim 1, wherein the slot includes an arcuate recess positioned adjacent to an inner surface of the base.

8. A spinal construct as recited in claim 1, wherein the second band is fixed with the second groove.

9. A spinal construct as recited in claim 1, wherein the second band includes a first mating surface engageable with a second mating surface of the second groove, the mating surfaces being engageable to fix the second band with the second groove.

10. A spinal construct as recited in claim 9, wherein the mating surfaces are engageable such that the second band axially translates relative to the base.

11. A spinal construct as recited in claim 9, wherein the mating surfaces are engageable to resist and/or prevent rotation of the second band relative to the base.

12. A spinal construct as recited in claim 1, wherein the second band is expandable between a provisional capture orientation and an expanded orientation, and a third band is disposed with the base and is expandable from a contracted orientation to an interference orientation to fix connection of the base and the shaft.

13. A spinal construct as recited in claim 12, further comprising a part disposed within the body and having a distal face engageable with the third band to fix the third band adjacent the second band.

14. A spinal construct comprising:
   a body defining a first groove and including a transverse rod formed therewith;
   a first band disposable in the first groove;
   a part disposed within the body;
   a base connectable with the body and engageable with the first band, the base defining a second groove and a slot;
   a second band disposable in the second groove and defining an opening aligned with the slot;
   a shaft connectable with the base and engageable with the second band, the shaft being configured to penetrate tissue, the opening being aligned with the slot to facilitate an angular range of movement of the shaft relative to the body; and
   a third band disposed with the base, the part being engageable with the third band to fix the base with the shaft.

15. A spinal construct as recited in claim 14, wherein the rod extends from the body at an angle of about 15 degrees relative to a transverse axis of the body.

16. A spinal construct as recited in claim 14, wherein the shaft is disposable in the slot to a selected angulation including an angular range of about 30 through about 60 degrees relative to a longitudinal axis of the body.

17. A spinal construct as recited in claim 16, wherein the selected angulation includes an angle of about 40 degrees relative to the longitudinal axis.

18. A spinal construct as recited in claim 14, wherein the second band is expandable between a provisional capture orientation and an expanded orientation, and the third band being expandable between a contracted orientation and an interference orientation to fix connection of the base and the second member.

19. A spinal construct as recited in claim 14, wherein the part includes a distal face engageable with the third band to fix the third band adjacent the second band.

20. A spinal construct comprising:
- a body having a spinal rod formed therewith, the body defining a first groove;
- a first band disposable in the first groove;
- a base connectable with the body and engageable with the first band, the base defining a second groove and a slot;
- a second band disposable in the second groove and defining an opening aligned with the slot; and
- a screw shaft connectable with the base and engageable with the second band in a non-instrumented assembly, the opening being aligned with the slot and the screw shaft being movable in the slot to a selected angulation including an angular range of about 30 through about 60 degrees relative to a longitudinal axis of the body.

* * * * *